(12) United States Patent
Dietsche et al.

(10) Patent No.: US 7,645,419 B2
(45) Date of Patent: Jan. 12, 2010

(54) KILLING MICROORGANISMS

(75) Inventors: Frank Dietsche, Schriesheim (DE);
Nathalie Bouillo, Baden-Baden (DE);
Karl Kolter, Limburgerhof (DE);
Christoph Hamers, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 882 days.

(21) Appl. No.: 10/529,629

(22) PCT Filed: Oct. 6, 2003

(86) PCT No.: PCT/EP03/11017

§ 371 (c)(1),
(2), (4) Date: Mar. 31, 2005

(87) PCT Pub. No.: WO2004/032628

PCT Pub. Date: Apr. 22, 2004

(65) Prior Publication Data

US 2006/0013724 A1 Jan. 19, 2006

(30) Foreign Application Priority Data

Oct. 7, 2002 (DE) .................................. 102 46 625

(51) Int. Cl.
*B08B 17/00* (2006.01)
*A61L 9/00* (2006.01)
*A61K 31/74* (2006.01)
*A61K 31/765* (2006.01)
*A01N 25/00* (2006.01)
*C08L 81/00* (2006.01)
*C08F 273/00* (2006.01)
*A01N 33/02* (2006.01)
*A01N 33/08* (2006.01)

(52) U.S. Cl. ................... 422/1; 422/6; 422/28; 422/32; 422/905; 424/78.08; 424/78.31; 424/78.32; 424/78.35; 424/78.37; 424/70.11; 424/405; 424/409; 525/328.2; 525/189; 525/291; 514/650; 514/653; 514/669

(58) Field of Classification Search .............. 422/1, 422/6, 28, 32, 905; 424/78.08, 78.31, 78.32, 424/78.35, 78.37, 70.11, 405, 409; 525/328.2, 525/189, 291; 514/650, 653, 669
See application file for complete search history.

(56) References Cited

U.S. PATENT DOCUMENTS

| 3,331,798 | A | | 7/1967 | Hibbard et al. |
| 3,907,720 | A | | 9/1975 | Field et al. |
| 4,036,788 | A | * | 7/1977 | Steckler ...................... 521/38 |
| 5,712,339 | A | * | 1/1998 | Guerin et al. ............... 524/515 |
| 5,882,677 | A | | 3/1999 | Kupperblatt |
| 5,922,776 | A | * | 7/1999 | Wellinghoff et al. ...... 514/772.3 |
| 6,040,406 | A | * | 3/2000 | Carrier et al. .......... 526/238.22 |
| 6,239,182 | B1 | | 5/2001 | Zaneveld et al. |
| 6,290,946 | B1 | | 9/2001 | Kurtz et al. |
| 6,458,348 | B1 | * | 10/2002 | Tropsch et al. ........... 424/78.35 |
| 6,482,392 | B1 | * | 11/2002 | Zhou et al. .................... 424/45 |
| 2001/0029287 | A1 | | 10/2001 | Loffler et al. |

FOREIGN PATENT DOCUMENTS

| CA | 2 383 030 | | 3/2001 |
| DE | 2001-235097/24 | | 3/2001 |
| EP | 0 130 789 | A1 | 1/1985 |
| GB | 2 072 508 | A | 10/1981 |
| JP | 54-157822 | | 12/1979 |
| JP | 2001-115135 | | 4/2001 |
| JP | 2001-343746 | | 12/2001 |
| WO | WO-92/05695 | | 4/1992 |
| WO | WO-02/49557 | A1 | 6/2002 |
| WO | WO-02/072020 | A2 | 9/2002 |

OTHER PUBLICATIONS

Tiller, et al;Designing Surfaces That Kill Bacteria On Contact (Proc. Natl. Acad. Sci. USA (2001)); vol. 98 (11); p. 5981-5985.

Schulz, et al.; Copolymers of N-Vinylpyrrolidone and Sulfonate Monomers; Exxon Research and Engineering Col, NJ;1989;pp. 165-174.

Ullmann's Enc. of Ind. Chem., 6th ed, 2000 Electronic Release "Microbiocides"-Introduction (Ken R. Payne and Edward Hill).

* cited by examiner

*Primary Examiner*—Jill Warden
*Assistant Examiner*—Monzer R Chorbaji
(74) *Attorney, Agent, or Firm*—Connolly Bove Lodge & Hutz LLP

(57) ABSTRACT

Described are a method of killing microorganisms in aqueous industrial systems or products for industrial applications based on water by adding from 0.001 to 5% by weight of a water-soluble or water-dispersible polymer containing from 30 to 100 mol % of styrenesulfonic acid, from 0 to 40 mol % of an N-vinyllactam and/or N-vinylamine, and from 0 to 30 mol % of further free-radically polymerizable monomers as biocidal additive, and a method of protecting articles by applying an antimicrobial aqueous composition comprising such an additive.

19 Claims, No Drawings

KILLING MICROORGANISMS

CROSS REFERENCE TO RELATED APPLICATION

The present application is a National Stage application of PCT/EP2003/011017, filed Oct. 6, 2003, which claims priority from German Patent Application No. DE 102 46 625.4, filed Oct. 7, 2002.

The invention relates to a method of killing microorganisms in aqueous industrial systems or products for industrial applications based on water by adding to the system from 0.001 to 5% by weight of a water-soluble or water-dispersible polymer containing from 30 to 100 mol % of styrenesulfonic acid, 0 to 40 mol % of an N-vinyllactam and/or N-vinylamine, and from 0 to 30 mol % of further free-radically polymerizable monomers as a biocidal additive. It further relates to a method of protecting articles by applying an antimicrobial, aqueous composition comprising such an additive.

The term microbiocide or biocide is used in a general sense for all substances having the capacity to kill microorganisms, and embraces antibiotics, chemotherapeutics, disinfectants, and fungicides. In a more specific sense the term embraces substances used in industrial or scientific applications for the purpose, for example, of preserving polymers, paints, inks, paper or wood or for protecting industrial installations such as cooling water circuits. Further details are set out in "Microbiocides", Ullmann's Encyclopedia of Industrial Chemistry, $6^{th}$ Edition, 2000 Electronic Release.

In industrial or scientific applications the normal requirements of a biocide, such as effective biocidal action without human toxicity, are accompanied by the requirement of very good performance properties. Biocides used in industrial applications ought not to impair the properties of the product under protection and ought to retain their effect in the product even in the course of its subsequent processing. Thus, for example, during the spray drying of an acrylic dispersion containing a biocide, the biocidal effect ought not to be impaired, so that even the dried powder or the redispersed powder is still protected by the biocide.

In aqueous dispersions, used for example to produce inks or coatings, it is common for the biocide used to comprise defined substances of low molecular mass such as bronopol (2-bromo-2-nitro-1,3-propanediol), for example. Bronopol, however, may give rise to a slight yellow shade. In certain applications, moreover, a low total halogen content is desirable in order to avoid corrosion and yellowing problems. Furthermore, high molecular mass biocides are advantageous in solid films in order to ensure a high long-term stability.

The use of polymers as biocides is known. For instance, DE-A 199 40 023, DE-A 199 52 221, and DE-A 199 55 992 disclose copolymers of aminopropyl vinyl ethers, acryloyloxyalkyldialkylamines or acryloyloxyalkylbenzophenone ammonium salts, in each case with other ethylenically unsaturated monomers, as microbial protection for various industrial applications or for the coating of surfaces. Cationic polymers of this kind, however, are incompatible with customary ionically stabilized acrylate dispersions.

It is also known that poly-4-styrenesulfonic acid or its salts can be used for various applications in the medical sector. U.S. Pat. No. 6,239,182 discloses the use of sodium polystyrenesulfonates as vaginal contraceptives or for use against HIV. U.S. Pat. No. 6,290,946 discloses the use of poly-4-styrenesulfonic acid or its derivatives in antibiotics. The use of polystyrenesulfonic acid and of styrenesulfonic acid copolymers as biocidal additives in the industrial sphere, on the other hand, has not been disclosed to date.

It is an object of the present invention to provide a method of killing microorganisms in an aqueous environment using polymers. Such a method ought also to be employable in ionically stabilized dispersions without thereby adversely affecting the properties of said dispersions.

We have found that this object is achieved by a method of killing microorganisms in aqueous industrial systems or products by adding to the system a biocidal additive, wherein the biocide is from 0.001 to 5% by weight of a water-soluble or water-dispersible polymer containing—based in each case on the total amount of all monomer units present in the polymer a) from 30 to 100 mol % of styrenesulfonic acid,
b) from 0 to 40 mol % of an N-vinyllactam and/or N-vinylamine, and
c) from 0 to 30 mol % of further free-radically polymerizable monomers and the sum of (a), (b), and (c) makes 100 mol %.

A second embodiment of the invention provides a method of protecting articles by applying an antimicrobial composition at least comprising water or a predominantly hydrous solvent mixture and a biocidal additive to the article by means of an appropriate technique and removing water or the predominantly hydrous solvent mixture, wherein the biocide is from 0.001 to 5% by weight of at least one water-soluble or water-dispersible polymer containing—based in each case on the total amount of all monomer units present in the polymer— a) from 30 to 100 mol % of styrenesulfonic acid,
b) from 0 to 40 mol % of an N-vinyllactam and/or N-vinylamine, and
c) from 0 to 30 mol % of further free-radically polymerizable monomers and the sum of (a), (b), and (c) makes 100 mol %.

Details of the invention follow.

The invention relates to the use of certain biocidal additives in the nonmedical sector. Therapeutic or medical applications in or on the human or animal body, and applications in crop protection, are not embraced by the present invention.

The term "aqueous industrial systems" for the purpose of this invention should be taken to include installations, especially chemical installations, manufacturing installations or machinery, in which water or predominantly aqueous mixtures are used as auxiliaries or reaction media. Examples include reaction vessels, storage vessels, heating vessels, water refrigeration circuits, heat exchanger circuits, utility water circuits, ballast water tanks or air conditioning units.

The term "products for industrial applications based on water" should be understood within the context of this invention to refer to water-based products which are employed in the industrial, scientific, commercial, workshop or household sectors. The term also covers the segment of the food industry.

The term "water-based" or "based on water" has the meaning, as known in principle, that the solvent or diluent medium used in the products is composed predominantly of water and that only small amounts of water-miscible or water-dispersible organic solvents are present in addition. With preference the solvent consists solely of water.

Examples of water-based products include, in particular, coating materials, impregnating materials, water-based varnishes or paints, printing inks, such as flexographic or inkjet inks, for example, dispersions such as acrylate or styrene-acrylate dispersions, for example, and also the formulations of such dispersions for use, for example, as wall paint, coating compositions, and textile auxiliaries. Further examples include polyurethane dispersions and their use, for example, to prepare transparent coating materials for wood, paper or coatings on plastic.

The polymeric biocidal additive employed in the method of the invention is a water-soluble or at least water-dispersible polymer. The polymer is preferably soluble in water.

As monomer (a) the polymer used in accordance with the invention contains from 30 to 100 mol % of styrenesulfonic acid, based on the sum of all the monomeric units. The monomer is preferably 4-styrenesulfonic acid, but can also be 2- or 3 styrenesulfonic acid or a mixture of the three isomers. With preference the polymer used in accordance with the invention contains from 30 to 98 mol % of styrenesulfonic acid, more preferably from 50 to 90 mol %, and very preferably from 60 to 8.0 mol %.

As comonomer (b) use is made of from 0 to 40 mol % of an N-vinyllactam and/or N-vinylamine. By way of example it is possible to use N-vinylpyrrolidone, N-vinylpiperidone, N-vinylcaprolactam or N-vinylformamide. Mixtures of different N-vinyllactams and/or different N-vinylamines can also be used. Preference is given to N-vinylpyrrolidone and N-vinylcaprolactam, particular preference to N-vinylpyrrolidone. The polymer used in accordance with the invention contains preferably from 2 to 40 mol % of the comonomer (b), more preferably from 3 to 30 mol %, and very preferably from 5 to 20 mol %.

As an option it is possible to use further comonomers (c) containing olefinically unsaturated groups, which can be polymerized by a free-radical method. Monomers of this kind serve to fine-tune the properties of the polymer. The nature and amount of any further monomer are selected by the skilled worker in accordance with the properties desired for the polymer. In principle it is possible to use any free-radically polymerizable monomers subject to the proviso that no unwanted properties result. In particular the polymer must remain soluble or dispersible in water. Monomer (c) preferably comprises derivatives of unsaturated carboxylic acids, such as (meth)acrylic esters, acrylamides or acrylonitrile. Examples include methyl(meth)acrylate, ethyl(meth)acrylate, n-propyl(meth)acrylate, isopropyl(meth)acrylate, lauryl(meth)acrylate, stearyl(meth)acrylate, and the esters of (meth)acrylic acid that derive from the isomeric butanols, and also hydroxyethyl(meth)acrylate, hydroxymethyl(meth)acrylate, hydroxypropyl(meth)acrylate, hydroxybutyl acrylate and hydroxybutyl(meth)acrylate. Suitable monomers further include unsaturated alcohols and amines and derivatives such as for example vinyl alcohol, vinyl acetate, vinyl propionate, vinyl stearate, vinyl benzoate, vinyl maleate, vinyl butyral, allyl phthalate, and allylmelamine. It is also possible, furthermore, to use ethylenically unsaturated hydrocarbons, such as ethylene, propylene or styrene, for example. It is of course also possible to use mixtures of different comonomers (c).

In one particular embodiment the comonomers (c) may be comonomers which in addition to an ethylenically unsaturated group contain crosslinkable groups. When comonomers of this kind are used the polymers obtained have additional functionalities which can be used for the purpose of crosslinking. One possible example in this case is acetoacetoxyethyl methacrylate.

The polymer used in accordance with the invention normally contains from 0 to 30 mol % of the comonomer (c), preferably from 1 to 20 mol %, and more preferably from 5 to 15 mol %.

The sum of the monomers (a), (b), and (c) present in the polymer amounts to 100 mol %.

The free-radical polymerization of the monomers presents no particular features and can be carried out in accordance with techniques known in principle to the skilled worker, for example, as an emulsion, dispersion or solution polymerization or inverse suspension polymerization or by polymerization in bulk. Preference is given to polymerization in solution, as described by EP-A 130 789 for example.

The weight average of the molecular weight is normally from 10 000 to 500 000 g/mol, although in certain cases good results may also be achieved outside of this range. The weight average is preferably from 15 000 to 300 000 g/mol and more preferably from 20 000 to 200 000 g/mol. The polydispersities $M_w/M_n$ are normally between 1.3 and 10 and are preferably <5 and more preferably <3. Nevertheless, acceptable results may still be achieved even outside of these ranges.

The polymers used for the method of the invention are water-soluble or water-dispersible. The sulfonic acid groups of the styrenesulfonic acid units in the polymer may be in the form of free acid groups. Alternatively some or all of them may be converted into salts. Alkali metal salts are preferred, and sodium salts particularly so. This also applies to any comonomers (c) in the polymer that contain acid groups.

The biocidal additive is added to aqueous industrial systems—that is, for example, to the refrigeration circuit or heat exchanger circuit, or else to the product, i.e., for example, to the aqueous dispersion. The additive can be added as it is. Preferably, however, it is the concentrates that are added. The skilled worker will also ensure that the biocide is distributed as uniformly as possible in the product or system under protection. The concentration used is guided by the desired end use and is chosen appropriately by the skilled worker. Thus for long-term prevention the skilled worker will generally use only a relatively small amount of the biocidal additive. Where a sudden infestation with microorganisms is to be controlled the skilled worker will select a higher concentration.

The biocidal additive is normally used in amounts of from 0.001 to 5% by weight. From 0.005 to 1% by weight is preferred, and from 0.01 to 0.5% by weight particularly preferred.

These concentrations refer to the use of the biocidal additive. It will be appreciated that concentrates of the polymer are preparable, too, which for use are first diluted to the desired concentration.

The water-soluble or water-dispersible polymers used in accordance with the invention can be employed as the sole biocidal additive. They are effective not only against bacteria but also against fungi and algae. Naturally, mixtures of different water-soluble or water-dispersible polymers as defined above can also be used. A further possibility is to use other biocidal additives or other auxiliaries, provided that no unwanted effects occur.

The polymers used in accordance with the invention are particularly suitable for protecting aqueous dispersions and products in which the aqueous dispersions are used. Examples of suitable dispersions include in particular dispersions based on acrylates, such as styrene acrylate dispersions, and also butadiene-styrene dispersions or polyurethane dispersions. The polymers can be added to such dispersions without giving rise to adverse effects. For example, the dispersions protected in accordance with the invention can be spray dried without substantially lessening the effect of the biocide.

The abovementioned polymer can also be utilized in a method of protecting articles by applying an antimicrobial, aqueous composition to the surface of the article.

The aqueous composition for coating comprises water or a predominantly hydrous solvent mixture, the biocidal additive outlined above, and, optionally, one or more binders and also further auxiliaries and additives.

"Predominantly hydrous" means that the greater part of the solvent mixture is composed of water and that only smaller amounts of one or more additional cosolvents are present, these amounts being not more than 25%, preferably not more than 15%, and very preferably not more than 5% by weight, based on the amount of all of the solvents. Suitable cosolvents ought to be miscible with water and can in particular be alcohols.

The biocidal additive is normally present in amounts of from 0.001 to 5% by weight. From 0.005 to 1% by weight is preferred, and from 0.01 to 0.5% by weight particularly preferred.

The composition preferably includes a binder. The binder can be a water-soluble binder. An example that may be mentioned is polyvinyl alcohol. Preferably, however, the binder is one which although not soluble in water is dispersible therein, such as an acrylate dispersion, for example.

The composition may further comprise suitable additives and auxiliaries, such as dispersing auxiliaries, further biocides, adhesion promoters or dyes, for example. It is prepared by thoroughly mixing all of the components of the composition with the solvent.

In particular the composition may also comprise a crosslinker or a system of crosslinkers. The nature of the crosslinker is dependent on the envisaged use of the composition. For example, the crosslinker can be one which triggers crosslinking on contact with atmospheric oxygen. Alternatively it may be a crosslinker system which can be cured thermally or photochemically. The components of the crosslinker may be present in the composition from the start. However, it is also possible not to add crosslinking components until shortly before the composition is used.

The composition is applied to the article to be protected, by coating, spraying or dipping, for example. The solvent is subsequently removed, generally simply by evaporation. If crosslinking is desired it can be triggered by irradiation or heating, or takes place as soon as the composition is applied to the article which is to be protected.

The composition can be used for coating for both indoor and outdoor applications. The additive does not alter the primary end properties of the coating, but merely makes the coating more stable in the long term to microbial, fungal and/or algal infestation.

The examples which follow illustrate the invention.

EXAMPLE 1

Test in a styrene/acrylate Dispersion

Test Procedure:

20 ml of each sample were inoculated with 0.2 ml of the individual microbial suspensions, homogenized, and incubated at 25° C. The microbe count was made immediately and after 14 and 28 days. This was done by plating out the inoculated sample in appropriate dilutions onto CASO agar with disinhibitor, using spatulas, or mixing the inoculated sample with the agar as a pour plate. The inoculated sample was diluted by homogenization with Caso broth+No. 3 and incubation for 30 minutes in a waterbath at 40° C. For detection of the bacteria, CASO agar plates were incubated at 30-35° C. for 3-5 days.

Testing Procedure:

For the tests the biocidal additive used was sodium polystyrenesulfonate with an $M_w$ of 20 000 g/mol.

A commercial aqueous styrene/n-butyl acrylate polymer dispersion with a solids content of 50%, a particle size of 170 nm, and a viscosity of 400 mPas (Acronal S 728 from BASF) was doped with either 500, 1000 or 2000 ppm of biocidal additive. Adding the biocide did not alter the properties of the dispersion. A microbial exposure test was carried out in accordance with the test procedure described above using *Escherichia coli*, *Pseudomonas aeruginosa*, and *Staphylococcus aureus*. The results are set out in table 1.

TABLE 1

Results of the tests of example 1

| Sample | Concentration of biocidal additive [ppm] | Time | Escherichia coli | Pseudomonas aeruginosa | Staphylococcus aureus |
|---|---|---|---|---|---|
| 0 | no biocide | 48 h | $10^4$ | $10^5$ | $10^5$ |
| 1 | 500 | 24 h | 6000 | 0 | 12000 |
| 2 | 500 | 48 h | 0 | 0 | 0 |
| 3 | 1000 | 24 h | 8000 | 0 | 12000 |
| 4 | 1000 | 48 h | 0 | 0 | 0 |
| 5 | 2000 | 24 h | 3600 | 100 | 8000 |
| 6 | 2000 | 48 h | 0 | 0 | 0 |

EXAMPLE 2

For the tests the biocidal additive used was sodium polystyrenesulfonate/N-vinylpyrrolidone (90/10) with an $M_W$ of 30 000 g/mol.

A microbe-free aqueous solution was dosed with either 10, 100 or 1000 ppm of the biocidal additive. A microbe exposure test was carried out in accordance with the test from Ph. Eur. 3, 2000 (5.1.3) using *Escherichia coli*, *Pseudomonas aeruginosa*, and *Staphylococcus aureus*. The results are set out in table 2. After 3 months at room temperature the samples were measured again, but no increase in the microbe count was found.

TABLE 2

Results of the tests of example 2

| No. | c [ppm] | pH | Escherichia coli | after 14 days | Pseudomonas aeruginosa | after 14 days | Staphylococcus aureus | after 14 days |
|---|---|---|---|---|---|---|---|---|
| 1 | 10 | 7 | $4.7 * 10^5$ | <10 | $4.7 * 10^5$ | <10 | $4.7 * 10^5$ | <100 |
| 2 | 100 | 7 | $2.3 * 10^5$ | <10 | $2.3 * 10^5$ | <10 | $2.3 * 10^5$ | <10 |
| 3 | 1000 | 7 | $1.4 * 10^5$ | <10 | $1.4 * 10^5$ | <10 | $1.4 * 10^5$ | <10 |

EXAMPLE 3

Spray Drying of a Dispersion

For the drying test the biocidal additive used was sodium polystyrenesulfonate/N-vinylpyrrolidone (95/5) with an $M_w$ of 20 000 g/mol in a 20% strength aqueous solution of a vinylpyrrolidone/vinyl acetate copolymer (monomer ratio about 55/65; Mw 45 000-70 000 g/mol) (Kollidon® VA 64, BASF AG).

The solution was processed in a one-nozzle spray dryer at entry temperatures of more than 140° C. The concentration of the polymeric biocide was found to be the same within the bounds of determination errors. A repeat inoculation as described in example 1 showed the biocidal activity to be unchanged.

TABLE 3

Results of example 3 (amounts in % by weight)

| | | | |
|---|---|---|---|
| Biocide concentration [%] | 0.01 | 0.1 | 1 |
| Residual moisture content [%] | 2.0 | 2.1 | 2.4 |
| Concentration in the powder [%] | 0.05 | 0.49 | 5.05 |
| Color | colorless | colorless | colorless |
| pH | 6.1 | 6.2 | 6.3 |
| Solids content [%] | 98 | 97.9 | 97.6 |

EXAMPLE 4

Test in Milk

A sample of milk was treated with 0.01% by weight of the sodium polystyrenesulfonate described in example 1. After 5 days of closed storage at room temperature the sample was still stable (microbe count, appearance, odor).

A comparative sample showed marked microbial infestation after just 24 hours of closed storage at room temperature.

We claim:

1. A method of killing microorganisms in aqueous systems or products based on water comprising adding a biocide to the system or product, wherein the biocide comprises from 0.001 to 5% by weight of at least one water-soluble or water-dispersible polymer comprising
   (a) from 30 to 98 mol % of styrenesulfonic acid,
   (b) from 2 to 40 mol % of an N-vinyllactam, and
   (c) from 0 to 30 mol % of free-radically polymerizable monomers, wherein the mol % is based on the total molar amount of monomer units present in the polymer, and the sum of (a), (b), and (c) totals 100 mol %.

2. A method as claimed in claim 1, wherein all or some of the sulfonic acid groups are in salt form.

3. A method as claimed in claim 1, wherein the products based on water are aqueous dispersions.

4. A method as claimed in claim 3, wherein the dispersion is electrostatically or ionically stabilized.

5. A method as claimed in claim 3, wherein the dispersion is spray dried.

6. A method as claimed in claim 1, wherein the aqueous systems are refrigeration or heat exchanger circuits.

7. A method as claimed in claim 1 wherein the water-soluble and water-dispersible polymer comprises 50 to 90 mol % styrenesulfonic acid, and 3 to 30 mol % N-vinyllactam.

8. A method as claimed in claim 7 wherein the free-radically polymerizable monomer is present from 5 to 15 mol %.

9. A method as claimed in claim 7 wherein the at least one water-soluble or water-dispersible polymer has a polydispersity $M_w/M_n$ from 1.3 to less than 3.

10. A method as claimed in claim 1 wherein the free-radically polymerizable monomers contain crosslinkable groups.

11. A method as claimed in claim 10 wherein the free-radically polymerizable monomer is acetoacetoxyethyl methacrylate.

12. A method of protecting articles by applying an antimicrobial composition comprising water or a predominantly hydrous solvent mixture and a biocide to the article and removing the water or the predominantly hydrous solvent mixture, wherein the biocide is from 0.001 to 5% by weight of at least one water-soluble or water-dispersible polymer comprising
   (a) from 30 to 98 mol % of styrenesulfonic acid,
   (b) from 2 to 40 mol % of an N-vinyllactam, and
   (c) from 0 to 30 mol % of free-radically polymerizable monomers, wherein the mol % is based on the total molar amount of all monomer units present in the polymer, and the sum of (a), (b), and (c) totals 100 mol %.

13. A method as claimed in claim 12, wherein the antimicrobial composition further comprises at least one binder.

14. A method as claimed in claim 12, wherein the antimicrobial composition further comprises a crosslinker or a system of crosslinkers.

15. A method as claimed in claim 12 wherein the water-soluble and water-dispersible polymer comprises 50 to 90 mol % styrenesulfonic acid, and 3 to 30 mol % N-vinyllactam.

16. A method as claimed in claim 15 wherein the free-radically polymerizable monomer is present from 5 to 15 mol %.

17. A method as claimed in claim 15 wherein the at least one water-soluble or water-dispersible polymer has a polydispersity $M_w/M_n$ from 1.3 to less than 3.

18. A method as claimed in claim 12 wherein the free-radically polymerizable monomers contain crosslinkable groups.

19. A method as claimed in claim 18 wherein the free-radically polymerizable monomer is acetoacetoxyethyl methacrylate.

* * * * *